United States Patent [19]

Tamai et al.

[11] Patent Number: 5,084,464
[45] Date of Patent: Jan. 28, 1992

[54] CONJUGATED γ-HYDROXYBUTENOLIDE COMPOUNDS AND ANTIULCER AGENTS CONTAINING THE SAME AS AN EFFECTIVE INGREDIENT

[75] Inventors: Yoshin Tamai, Shibata; Masahiro Torihara, Kurashiki; Yoichi Kido, Ichikawa; Johji Yamahara, Ootsu, all of Japan

[73] Assignee: Kuraray Company Ltd., Kurashiki, Japan

[21] Appl. No.: 583,946

[22] Filed: Sep. 13, 1990

[30] Foreign Application Priority Data

Sep. 20, 1989 [JP] Japan .................. 1-245754

[51] Int. Cl.⁵ .................. A61K 31/44; C07D 401/06
[52] U.S. Cl. .................. 514/336; 514/444; 514/473; 514/471; 546/283; 549/60; 549/313; 549/320
[58] Field of Search .................. 549/313, 320, 60; 514/444, 473, 336, 471; 546/283

[56] References Cited

U.S. PATENT DOCUMENTS

| | | | |
|---|---|---|---|
| 4,797,417 | 1/1989 | Okamoto et al. | 549/313 |
| 4,950,818 | 8/1990 | Tamai et al. | 514/473 |

FOREIGN PATENT DOCUMENTS

| | | | |
|---|---|---|---|
| 0209274 | 1/1987 | European Pat. Off. | 514/473 |
| 0212578 | 9/1986 | Japan | 549/320 |
| 2164676 | 7/1987 | Japan | 549/313 |

Primary Examiner—Jane T. Fan
Assistant Examiner—Amelia A. Owens
Attorney, Agent, or Firm—Oblon, Spivak, McClelland, Maier & Neustadt

[57] ABSTRACT

The present invention provides conjugated γ-hydroxybutenolide compounds represented by the general formula:

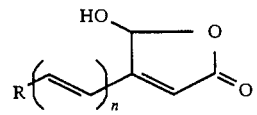

wherein R represents, when n is 1, furyl groups, thienyl groups or naphthyl groups, unsubstituted or substituted with alkyl group or alkoxy group; phenyl groups substituted with dialkylamino group, acyl group or pyridinyl group; or

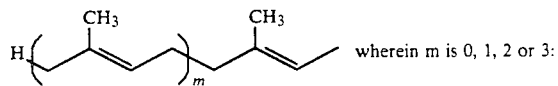

wherein m is 0, 1, 2 or 3:

when n is 2 or 3, phenyl groups unsubstituted or substituted with alkyl group or alkoxy group; and antiulcer agents comprising an aforementioned conjugated γ-hydroxybutenolide compound as an active ingredient.

10 Claims, No Drawings

CONJUGATED γ-HYDROXYBUTENOLIDE COMPOUNDS AND ANTIULCER AGENTS CONTAINING THE SAME AS AN EFFECTIVE INGREDIENT

BACKGROUND OF THE INVENTION

1. Field of the Invention

The present invention relates to conjugated γ-hydroxybutenolide compounds and antiulcer agents containing the same as an effective ingredient.

2. Description of the Prior Art

It has been known that the following conjugated γ-hydroxybutenolide compounds have a cell-killing activity on mouse neuroblastoma N18TG-2 (Int. J. Cancer, 33, 677 (1984)).

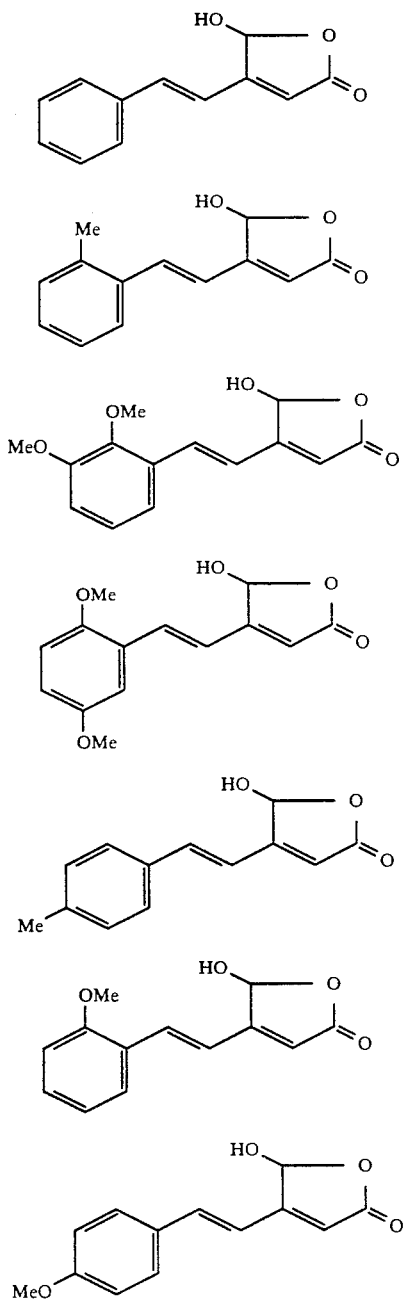

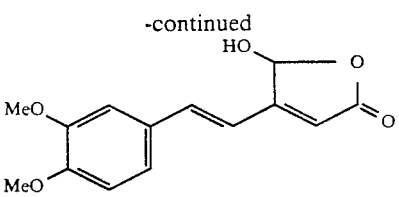

However, there has never so far been known the usefulness of these compounds as a therapeutic agent for peptic ulcers.

SUMMARY OF THE INVENTION

The present inventors have investigated pharmacological activities other than antitumor activity of conjugated γ-hydroxybutenolide compound, and as a result have found that conjugated γ-hydroxybutenolide compounds represented by the following general formula (I) have a high antiulcer activity against peptic ulcers and have accomplished the present invention.

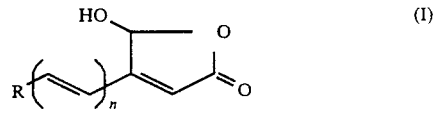

wherein R represents, when n is 1, furyl groups, thienyl groups or naphthyl groups, unsubstituted or substituted with alkyl group or alkoxy group; phenyl groups substituted with dialkylamino group, acyl group or pyridinyl group; or

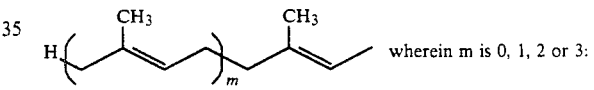

when n is 2 or 3, phenyl groups unsubstituted or substituted with alkyl group or alkoxy group.

Further, the conjugated γ-hydroxybutenolide compounds of the general formula (I) are new compound nondescribed in literature.

DESCRIPTION OF THE PREFERRED EMBODIMENTS

In the above mentioned general formula (I), as substituent, the alkyl group includes lower alkyl groups having 1 to 15 carbon atoms prefereably 1 to 4 carbon atoms such as a methyl, ethyl, n-propyl, i-propyl, n-butyl, sec-butyl, t-butyl group and the like; the alkoxy group includes lower alkoxy groups such as a methoxy, ethoxy, propoxy, isopropoxy, butoxy group and the like; the dialkylamino group includes a dimethylamino, diethylamino group and the like; and the acyl groups includes an acetyl, propionyl, butyryl, isobutyryl, valeryl, benzoyl group and the like.

Examples of the conjugated γ-hydroxybutenolide compounds represented by the general formula (I) are enumerated below, and each compound number therein is consistently used hereinafter as indicating just the compound:

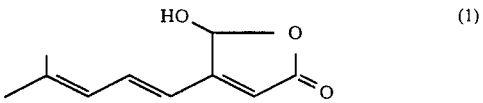

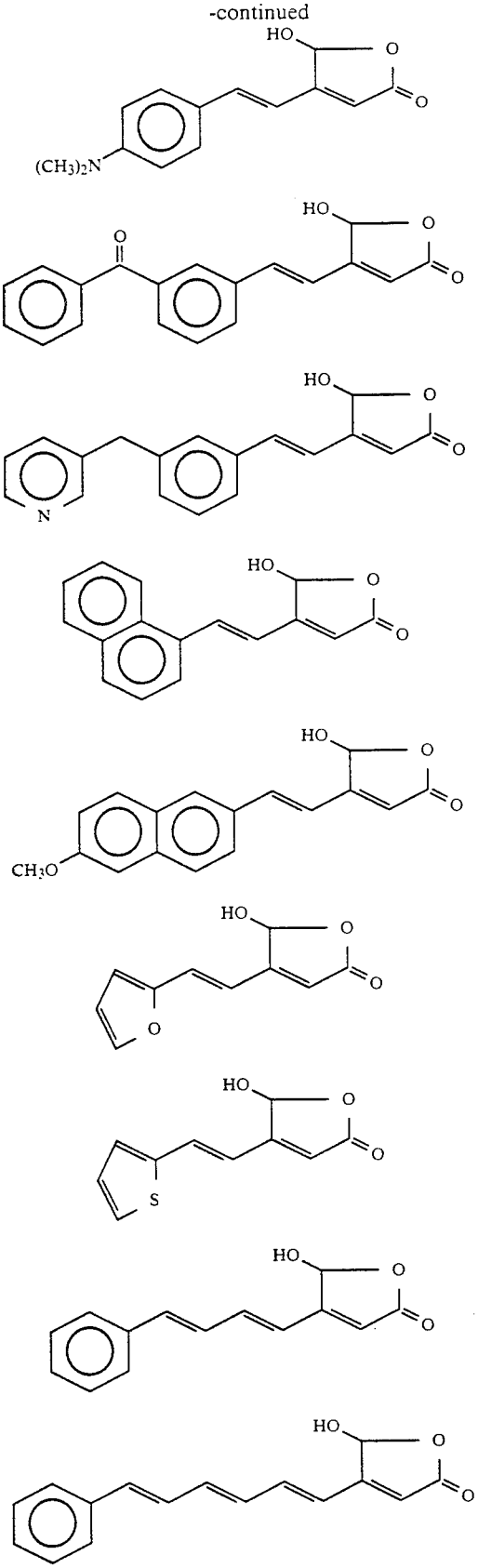

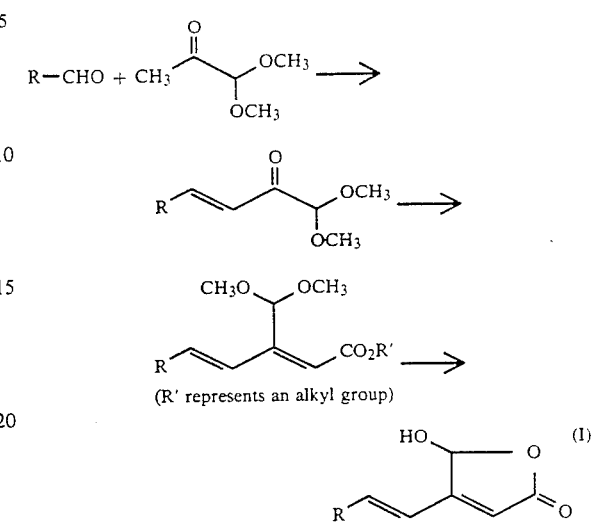

(R' represents an alkyl group)

5-hydroxy-4-[2-phenyl-(E)-ethenyl]-2(5H)-furanone (Chem. Pharm. Bull. 34 (10), 4346 (1986)).

This reaction is indicated by the following steps:

Conjugated γ-hydroxybutenolide compounds represented by the general formula (I) can be prepared in a manner analogous to the preparation method of known That is, an aldehyde is reacted with pyruvic aldehyde dimethyl acetal in methanol as a solvent in the presence of a base, for example an alkali such as sodium hydroxide, potassium hydroxide and barium hydroxide, or an organic base such as DBU (1,8-diazabicyclo(5,4,0)undecene-7), pyridine, pyperidine and triethylamine, at a temperature of 0° to 65° C. (reflux temperature of methanol) for a period of 1 to 10 hours to synthesize (E)-1,1-dimethoxy-4-substituted-3-butene-1-one.

Purification can be carried out by adding water after the completion of the reaction, extracting with n-hexane or ether, washing the separated organic solvent layer with water and distilling away the organic solvent therefrom. The resulting compound is reacted with a phosphoric acid ester according to Emmons-Horner reaction to obtain a 3-dimethoxymethyl-5-substituted-2,4-pentadienyl carboxylic acid alkyl ester.

This reaction is carried out using conventional conditions for Emmons-Horner reaction, for example using n-BuLi, NaH, NaOMe, NaOEt and the like as a base and benzene, toluene, tetrahydrofuran and the like as a solvent inert to the reaction at around room temperature for a period of 1 to 24 hours. Purification can be carried out by pouring the reaction solution after the completion of the reaction into water, extracting with ether, washing the organic solvent layer with water and distilling off the ether.

The thus obtained unsaturated ester is then treated with an aqueous sulfuric acid solution of 20 to 50% at a temperature of room temperature to 50° C. for a period of 1 to 10 hours to obtain a desired conjugated γ-hydroxybutenolide compound. In this reaction, iodine may be added to the reaction solution in an amount of 0.01 to 1.0 percent by weight as a reaction accelerator. Purification can readily be carried out by column chromatography or recrystallization.

The present invention relates to an antiulcer agent comprising as an effective ingredient a conjugated γ-hydroxybutenolide compound represented by the general formula (I), and such antiulcer agents may be the form of tablets, capsules, powders, granules, electuaries, or liquid preparation such as sterile solution and suspensions for oral or parenteral administration.

Tablets, granules and powders are suitable for orally administering active ingredients of the present invention, and granules and powders can, if necessary, be formulated into capsules as a unit dose form.

Solid agents for oral administration may contain conventional excipients such as silicon oxide, synethetic aluminum silicate, lactose, sucrose, corn starch and microcrystalline cellulose; binders such as gum arabic, gelatin and polyvinylpyrrolidone; lubricants such as magnesium stearate, talc and silica; disintegrants such as potato starch and carboxymethylcellulose calcium; wetting agents such as polyethylene glycol, sorbitan mono-oleate or sodium lauryl sulfate. Tablets may be coated according to a conventional method.

Liquid preparations for oral administration may be aqueous or oily suspensions, solutions, syrups, etc., or may be dry preparation which can be dissolved again in a suitable vehicle prior to use. Such liquid preparations may contain conventional emulsifiers such as lecithin and sorbitan mono-oleate; emulsification aids such as sorbitol syrup, methylcellulose and gelatin; non-aqueous vehicles such as coconut oil and peanut oil; antioxidants; coloring agents; flavoring agents; etc.

For use in parenteral administration, a conjugated γ-hydroxybutenolide compound of the general formula (I) may be dissolved or suspended in a sterile vehicle to obtain a liquid preparation. The preparation of the solution may be carried out by dissolving an active compound in a vehicle for injection, filtering the solution for sterility, and pouring the solution into ampules and sealing them.

In the preparation it is preferable to add adjuvants such as local anesthetics, antiseptics and buffering agents in the vehicle. The suspension can be prepared in substantially the same manner as in the preparation of the solution except that an active compound is not dissolved but suspended in a vehicle and a procedure for sterility other than filteration is used.

Pharmaceutical compositions comprising a conjugated γ-hydroxybutenolide compound of the general formula (I) of the present invention as an active ingredient are effective for treatment and/or prevention of ulcers of digestive organs, particularly stomach of human beings.

Although the effective amount or dose of the compounds varies depending on the extent of ulcers, the status of patients, kind of compounds of the general formula (I) to be used, etc., proper doses generally in the range from about 100 to about 2500 mg per day for adult use.

[EXAMPLES]

Examples of the present invention are indicated below.

REFERENCE EXAMPLE 1

Synthesis of
5-hydroxy-4-[4-methyl-1,3-pentadienyl]-2(5H)-furanone (Compound(1))

0.94 g (23.5 mmole) of sodium hydroxide was dissolved in 500 g of methanol, and 40 g (0.47 mole) of senecioaldehyde and 110 g (0.94 mole) of pyruvic aldehyde dimethyl acetal were added to the solution, and the mixture was stirred at room temperature for 2 hours.

After the completion of the reaction, 200 g of water was added thereto, and the mixture was extracted three times with each 500 ml of n-hexane. The n-hexane layer was concentrated in an evaporator to obtain 65.9 g of the crude residue.

Thereafter, 20.7 g (0.52 mole) of sodium hydride was added to 200 g of toluene, followed by ice-cooling to maintain the inner temperature at 5° to 15° C., and this mixture a solution prepared by diluting 124 g (0.55 mole) of triethyl phosphonoacetate with 100 g of toluene was added in dropwise for a period of one hour. After the completion of dropwise addition, the mixture was warmed to room temperature and stirred for an additional hour. A solution prepared by diluting 65.9 g of the previously prepared crude 1,1-dimethoxy-6-3,5-heptadiene-2-one with 100 g of toluene was then added dropwise thereto for a period of 2 hours. After the completion of dropwise addition, the mixture was stirred for an additional hour and let to stand overnight.

300 ml of 10% ammonium chloride solution was added to the reaction mixture, and the mixture was twice extracted with each 500 ml of isopropyl ether. The isopropyl ether layer was washed twice with each 300 ml of 10% aqueous sodium chloride solution and the isopropyl ether was removed by evaporation using an evaporator to obtain 121.2 g of the residue.

After 121.2 g of this residue was dissolved in 500 ml of dioxane, 1 g of iodine and 150 ml of 30% aqueous sulfuric acid solution were added to the solution, and the mixture was refluxed with heating under stirring for 1 hour. After the completion of the reaction, the mixture was extracted twice with each 500 ml of isopropyl ether. The isopropyl ether layer was washed with 1 liter of saturated aqueous sodium chloride solution and isopropyl ether was removed by evaporation using an evaporator. The obtained residue was purified by a silica column chromatography with an effluent solvent consisting of n-hexane and ethyl acetate in a ratio of 3 to 1. The obtained oil was recrystallized from the mixed solvent of n-hexane and ethyl acetate to obtain 4.5 g of yellow crystal.

It was confirmed by $^1$H-NMR that these crystals were 5-hydroxy-4-[4-methyl-1,3-pentadienyl]-2(5H)-furanone.

$^1$NMR (60 MHz, Acetone-$d_6$/TMS): 1.90 (s, 6H), 5.96 (s, 1H), 6.40 (s, 1H), 6.1–6.6 (dx2,2H), 6.80 (brs, 1H, —OH), 7.35 (dd, 1H).

IR (KBr): 3240 (OH), 1720 ($\alpha,\beta$-unsaturated γ-lactone), 1620 (C=C).

EXAMPLE 2-10

Various conjugated γ-hydroxybutenolide compound prepared in the same manner as Example 1 and the $^1$H-NMR spectra and infrared absorption spectra are shown in Table 1.

TABLE 1

| Compounds | ¹H-NMR (d₆-acetone) and/or d₆-DMSO) | IR(KBr) |
|---|---|---|
| (1) [structure: 5-(4-methylpenta-1,3-dienyl)-4-hydroxy-α,β-unsaturated γ-lactone] | δ = 1.90 s 6H(CH₃ × 2)<br>δ = 5.96 s 1H(a)<br>δ = 6.40 s 1H(b)<br>δ = 6.1~6.6 d × 2 2H(c, e)<br>δ = 6.80 brs 1H (OH)<br>δ = 7.35 dd 1H (d) | 3240(OH)<br>1720<br>(α, β-unsaturated γ-lactone)<br>1620(C=C) |
| (2) [structure with (CH₃)₂N-phenyl-styryl-lactone] | δ = 2.90 s 6H(CH₃ × 2)<br>δ = 5.90 s 1H(a)<br>δ = 6.25 brs 1H(b)<br>δ = 6.4~7.7 m 7H<br>(c, d, OH and arom H) | 3230(OH)<br>1710<br>(α, β-unsaturated γ-lactone)<br>1580(C=C)<br>1330(Aromatic tertiary amine) |
| (3) [structure: benzoyl-phenyl-styryl-lactone] | δ = 6.25 s 1H(a)<br>δ = 6.55 brs 1H(b)<br>δ = 6.95 brs 1H(OH)<br>δ = 7.4~8.1 m 11H<br>(c, d and arom H) | 3250(OH)<br>1760 (Aromatic ketone)<br>1720<br>(α, β-unsaturated γ-lactone)<br>1630, 1660(C=C) |
| (4) [structure: pyridylmethyl-phenyl-styryl-lactone] | δ = 4.08 s 2H(e)<br>δ = 6.15 s 1H(a)<br>δ = 6.50 s 1H(b)<br>δ = 7.2~8.6 m 11H<br>(OH, c, d and arom H) | 3100(OH)<br>1760<br>(α, β-unsaturated γ-lactone)<br>1590, 1620(C=C) |
| (5) [structure: naphthyl-vinyl-lactone] | δ = 6.30 s 2H(a)<br>δ = 6.55 s 1H(b)<br>δ = 6.9~8.4 m 10H<br>(OH, c, d and arom H) | 3280(OH)<br>1730<br>(α, β-unsaturated γ-lactone)<br>1620(C=C) |
| (6) [structure: methoxynaphthyl-vinyl-lactone] | δ = 3.95 s 3H(CH₃O—)<br>δ = 6.15 s 1H(a)<br>δ = 6.45 brs 1H(b)<br>δ = 6.75 brs 1H(OH)<br>δ = 6.8~8.0 m 8H<br>(c, d and arom H) | 3400(OH)<br>1760<br>(α, β-unsaturated γ-lactone)<br>1610(C=C) |
| (7) [structure: furyl-dienyl-lactone] | δ = 6.10 s 1H(a)<br>δ = 6.40 s 1H(b)<br>δ = 7.35 s 1H(OH)<br>δ = 7.0, 7.1 s × 2 2H(c, d)<br>δ = 6.6 dd 1H ⎫<br>δ = 6.8 d 1H ⎬ (arom H)<br>δ = 7.7 d 1H ⎭ | 3250(OH)<br>1730<br>(α, β-unsaturated γ-lactone)<br>1605, 1620(C=C)<br>950(Mono-substituted furan) |
| (8) [structure: thienyl-dienyl-lactone] | δ = 6.10 s 1H(a)<br>δ = 6.45 brs 1H(b)<br>δ = 6.80 brs 1H(OH)<br>δ = 7.0~7.9 m 5H<br>(c, d, and arom H) | 3220(OH)<br>1730<br>(α, β-unsaturated γ-lactone)<br>1610(C=C)<br>960(Mono-substituted thiophene) |
| (9) [structure: phenyl-trienyl-lactone] | δ = 6.10 s 1H(a)<br>δ = 6.40 brd 1H(b)<br>δ = 6.7~7.8 m 10H<br>(c, d, e, f, OH and arom H) | 3250(OH)<br>1720<br>(α, β-unsaturated γ-lactone)<br>1590, 1600(C=C) |

TABLE 1-continued

| Compounds | $^1$H-NMR (d$_6$-acetone) and/or d$_6$-DMSO) | IR(KBr) |
| --- | --- | --- |
| (10) | δ = 6.10 s 1H(a)<br>δ = 6.40 brs 1H(b)<br>δ = 6.6~7.8 m 12H<br>(c~h, OH and arom H) | 3250(OH)<br>1740<br>(α, β-unsaturated γ-lactone)<br>1570, 1580, 1600<br>1620(C=C) |

EXAMPLE 11

Antiulcer Activity (HCl-Ethanol Ulcer)

1.5 ml of a 60% aqueous ethanol solution containing 150 mM hydrochloric acid was orally administered to rats. One hour thereafter the rats were sacrificed and the length (mm) of HCl-ethanol-induced ulcers generated at the mucosa of the stomach were measured. Sum of the length of ulcer per animal is defined as ulcer coefficient. Specimens each was orally administered one hour before the HCl-ethanol administration. Inhibition rate was calculated as the ratio of the difference of ulcer coefficients of the control group and specimen-administered group to the ulcer coefficient of the control group. The results were as shown in Tables 2-1 and 2-2.

TABLE 2-1

| Example No. | Compound | Dose (mg/kg) | Animal No. | Inhibition Rate (%) |
| --- | --- | --- | --- | --- |
|  | Control | — | 7 | — |
| 1 | (1) | 5 | 6 | 90.6 |
| 2 | (2) | 2.5 | 6 | 37.5 |
| 3 | (3) | 5 | 6 | 69.7 |
| 4 | (4) | 5 | 6 | 42.0 |
| 5 | (5) | 2.5 | 6 | 94.0 |
| 6 | (6) | 5 | 6 | 61.3 |
| 7 | (7) | 2.5 | 6 | 96.0 |
| 8 | (8) | 2.5 | 6 | 95.5 |
| 9 | (9) | 5 | 6 | 98.6 |
| 10 | (10) | 5 | 6 | 61.8 |

TABLE 2-2

| Comparative Example No. | Compound | Dose (mg/kg) | Animal No. | Inhibition Rate (%) |
| --- | --- | --- | --- | --- |
| 1 | Spizofurone | 100 | 5 | 86.6 |
| 2 | Teprenone | 25 | 5 | 48.9 |

Spizofurone

Teprenone

Both are typical antiulcer agents.

EXAMPLE 12

Acute Toxicity

Acute toxicity tests through oral administration were carried out using male ICR-strain mice (5 weeks old). The LD$_{50}$ value of 5-hydroxy-4-[4-methyl-1,3-pentadienyl]-2(5H)-furanone of the present invention was 2000 mg/kg or more, and thus the compound was ascertained to have higher safety in comparison with effective amount.

EXAMPLE 13

Drug Suitable for Oral Administration

The following components were mixed and the mixture was formulated with a tabletting machine into tablets.

| Component | Weight per tablet (mg) |
| --- | --- |
| Compound (1) | 100 |
| Corn starch | 50 |
| Microcrystalline cellulose | 100 |
| Carboxymethylcellulose | 50 |
| Total | 300 |

EXAMPLE 14

Capsule for use in Oral Administration

The following components were mixed in a conventional manner and this mixture was filled into hard gelatin to prepare capsules

| Component | Weight per capsule (mg) |
| --- | --- |
| Compound (1) | 50 |
| Neusilin ® | 150 |
| Corn starch | 100 |
| Total | 300 |

What is claimed is:

1. Conjugated γ-hydroxybutenolide compounds represented by the general formula:

groups, or naphthyl groups, unsubstituted or substituted with C$_{1-15}$alkyl group or C$_{1-15}$alkoxy group; phenyl groups substituted with di(C$_{1-15}$)alkylamino group, acyl group or pyridinyl group; or wherein m is 0, 1, 2 or 3:

wherein m is 0, 1, 2 or 3: when n is 2 or 3, phenyl groups unsusbstituted or substituted with C$_{1-15}$alkyl group or C$_{1-15}$alkoxy group.

2. The compound of claim 1, wherein n is 2 or 3, and R is a phenyl group substituted with an alkoxy group.

3. The compound of claim 1, wherein the alkyl group, alkoxy group and dialkylamino group are of C$_{1-4}$ content.

4. An antiulcer pharmaceutical composition which comprises an effective amount of at least one of the conjugated γ-hydroxybutenolide compounds represented by the general formula:

$$\text{structure}$$

wherein R represents, when n is 1, furyl groups, thienyl groups or naphthyl groups, unsubstituted or substituted with $C_{1-15}$alkyl group or $C_{1-15}$alkoxy group; phenyl groups substituted with di($C_{1-15}$)alkylamino group, acyl group or pyridinyl group; or

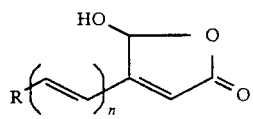 wherein m is 0, 1, 2 or 3;

when n is 2 or 3, phenyl groups unsubstituted or substituted with $C_{1-15}$alkyl group or $C_{1-15}$alkoxy group; and at least one pharmaceutically acceptable carrier.

5. A composition of claim 4 wherein the ulcer is the ulcer of stomach.

6. The composition of claim 4, wherein n is 2 or 3, and R is a phenyl group substituted with an alkoxy group.

7. The composition of claim 4, wherein the alkyl group, alkoxy group and dialkylamino group are of $C_{1-4}$ content.

8. A method of treating ulcers of the stomach in a patient in need thereof, which comprises administering to the patient an effective amount of the compound of claim 1.

9. The method of claim 8, wherein n is 2 or 3, and R is a phenyl group substituted with an alkoxy group.

10. The method of claim 8, wherein the alkyl group, alkoxy group and dialkylamino group are of $C_{1-4}$ content.

* * * * *